United States Patent [19]

Fields, Jr. et al.

[11] Patent Number: 4,810,426

[45] Date of Patent: Mar. 7, 1989

[54] PROCESS FOR MAKING GLYPHOSATE FROM N-PHOSPHONOMETHYL-2-OXAZOLIDONE

[75] Inventors: Donald L. Fields, Jr., St. Louis; Len F. Lee, St. Charles; Thomas J. Richard, University City, all of Mo.

[73] Assignee: Monsanto Company, St. Louis, Mo.

[21] Appl. No.: 823,178

[22] Filed: Jan. 28, 1986

[51] Int. Cl.$^4$ .................................................. C07F 9/38
[52] U.S. Cl. .......................... 260/502.5 F; 260/502.5 E
[58] Field of Search ..................... 260/502.5 F; 562/539

[56] References Cited

U.S. PATENT DOCUMENTS

| | | | |
|---|---|---|---|
| 2,824,130 | 2/1958 | Robertson et al. | 562/539 |
| 3,404,179 | 10/1968 | Weiss et al. | 562/539 |
| 4,427,599 | 1/1984 | Felix | 260/502.5 F |
| 4,442,041 | 4/1984 | Subramanisn | 260/502.5 F |
| 4,547,324 | 10/1985 | Wong et al. | 260/502.5 F |

FOREIGN PATENT DOCUMENTS

| | | | |
|---|---|---|---|
| 97522 | 1/1984 | European Pat. Off. | 260/502.5 F |
| 76493 | 10/1970 | German Democratic Rep. | 562/539 |
| 96516 | 7/1975 | Japan | 562/539 |
| 601816 | 5/1948 | United Kingdom | 562/539 |
| 601817 | 5/1948 | United Kingdom | 562/539 |
| 1047555 | 11/1966 | United Kingdom | 562/539 |

*Primary Examiner*—J. E. Evans
*Attorney, Agent, or Firm*—Frank D. Shearin; David Bennett

[57] ABSTRACT

Hydrolysis of N-phosphonomethyl-2-oxazolidone and separation of the carbon dioxide co-product prior to oxidation of the hydrolyzate to glyphosate results in a process of significantly increased efficiency over the previously described processes.

9 Claims, No Drawings

PROCESS FOR MAKING GLYPHOSATE FROM N-PHOSPHONOMETHYL-2-OXAZOLIDONE

BACKGROUND TO THE INVENTION

The present invention relates to a process for producing N-phosphonomethylglycine and specifically to a process in which the starting material is N-phosphonomethyl-2-oxazolidone.

U.S. Pat. No. 4,547,324 discloses a process for producing N-phosphonomethylglycine by a process in which N-phosphonomethyl-2-oxazolidone is reacted with an aqueous solution of alkali metal hydroxide in the presence of cadmium oxide as a catalyst and thereafter acidifying the reaction product to generate the acid.

Reproduction of the only example provided in U.S. Pat. No. 4,547,324 gave a relatively low yield, (40.2%), of glyphosate. The process as described in the above patent is, therefore, somewhat inefficient. In addition it permits the use of only cadmium oxide as catalyst.

A process has now been discovered that improves significantly on the process in U.S. Pat. No. 4,567,324 permitting an improved yield and reduced reactant requirements and a broader selection of catalysts.

DESCRIPTION OF THE INVENTION

The process of the invention comprises heating an aqueous solution of N-phosphonomethyl-2-oxazolidone so as to bring about hydrolysis of the oxazolidone group and formation of gaseous carbon dioxide; continuing the reaction till the oxazolidone has been substantially completely converted to N-phosphonomethylethanolamine or the cyclic internal ester thereof and removing the carbon dioxide co-product; thereafter oxidizing the hydrolyzate by adding a greater than one molar excess, after neutralization of acid group in the phosphonomethyl group, of an aqueous alkali and a catalyst selected from cadmium, zinc, copper, palladium and platinum and their respective oxides, hydroxides and salts; heating at a temperature of 200° to 300° C.; and acidifying the reaction mixture so as to generate N-phosphonomethylglycine.

It will be seen that the above process differs from that of U.S. Pat. No. 4,547,324 not only in the fact that it produces an improved yield, but also in that the hydrolysis of the oxazolidone compound is carried out before the oxidation reaction. This is a most important difference because it has been found that the hydrolysis of the oxazolidone is accompanied by the evolution of carbon dioxide under neutral or acidic conditions. If the hydrolysis and oxidation reactions are carried out simultaneously in the same reaction vessel as described in the above patent, the carbon dioxide reacts with the alkali to form a carbonate and this is found to have an adverse effect on the rate and yield of the reaction. In addition, this reaction uses up alkali such that a larger amount is required to accomplish the oxidation reaction. By hydrolyzing the oxazolidone so as to liberate gaseous carbon dioxide before adding the alkali and the oxidation catalyst, the formation of an inhibitor that subsequently reduces the efficiency of the catalyst is avoided. In addition, the waste of two equivalents of alkali (that react with the carbon dioxide to form the alkali metal carbonate) is eliminated and consequently there is a saving of two equivalents of acid in the subsequent acidification step. Furthermore, two equivalents fewer of salt are generated in the neutralization step. This lower salt load significantly reduces the volume of waste from this process.

It is possible to conduct the reaction in the presence of catalytic amount of an acid with a non-nucleophilic anion, such as sulphuric acid, but this, of course, does not take full advantage of the potential for saving in the amount of alkali needed in the reaction because this catalytic amount of acid will need to be neutralized before the subsequent oxidation step.

The objectives of the invention are achieved preferably by hydrolyzing the oxazolidone in water and, only after evolution of carbon dioxide has ceased and been removed, adding the alkali and the catalyst to perform the oxidation reaction. The preparation of the oxazolidone derivative is described in U.S. Pat. No. 4,547,324 and involves the reaction of 2-oxazolidone with paraformaldehyde followed by reaction with, for example, phosphorous trichloride in a carboxylic acid solvent at an elevated temperature.

The hydrolysis reaction can be conducted in an autoclave at a temperature of 100° to 300° C. Preferably, however, a temperature of 175° to 250° C. is found to be adequate. The carbon dioxide generated must of course, be removed from the reactor before the alkali and catalyst are added for the oxidation reaction. As is obvious to anyone skilled in the art, this removal can be accomplished by any number of techniques, among which are reactor venting and/or an inert gas purge.

The hydrolysis reaction is found to result in the production of N-phosphonomethylethanolamine and its cyclic internal ester with the formula

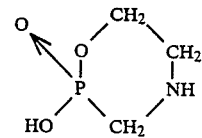

Under the conditions of the oxidation step this cyclic internal ester is transformed into the desired N-phosphonomethylglycine as well as its acyclic precursor.

The oxidation reaction to yield an N-phosphonomethylglycine salt occurs when the N-phosphonomethylethanolamine (or its cyclic internal ester) reacts with an alkali in the presence of water and a suitable catalyst at an elevated temperature. The reaction temperature can be from about 150° C. to about 300° C. It is found, however, that higher temperatures can increase the incidence of side reactions so that the preferred oxidation reaction temperature is about 200° to 250° C. The reaction is most conveniently carried out in an autoclave under autogenous pressure. This may in fact be the same reactor as that in which the hydrolysis reaction was performed.

The catalyst is preferably selected from cadmium, zinc, copper, platinum and palladium oxides though cadmium oxide is the most preferred catalyst. It should be noted that the corresponding finely divided metals or salts of such metals can also be used as catalysts in this reaction. In certain instnces, it may be advantageous to use these catalysts on inert supports like activated carbon or other commercially available supports. The general scope of catalysts available for this oxidation is another feature distinguishing this process from U.S. Pat. No. 4,547,324 which permits only cadmium oxide as catalyst. The adverse effects of alkali metal carbonate formed in situ would appear to contribute to this limited choice of catalysts.

The alkali can be any one of the hydroxides of the alkali metals but for several reasons, potassium hydroxide and especially sodium hydroxide are the preferred reactants.

The alkali is present in a greater than one molar excess after acid-group neutralization has occurred and this is intended to ensure that the amount added exceeds that required to neutralize any acid functionalities in the hydrolyzate and to form the sodium salt of the product. The molar ratio of alkali to ethanolamine derivative after acid group neutralization is preferably from 1.5:1 to 6:1 and specifically from 1:5 to 4:1. The strength of the alkali in the reaction mixture (after neutralization has occurred) is most suitably from 10% to 50% with from 15% to 30% being especially preferred.

After completion of the oxidation the reaction product is in the form of the alkali metal salt of N-phosphonomethylglycine. The free acid can, of course, be obtained by any of a number of methods obvious to those skilled in the art, one example of which is the acidification/crystallization at or near the isoelectric point.

The invention is further described in the following Examples which are designed merely to illustrate embodiments of the invention and to point up the advantages of the invention over that described in U.S. Pat. No. 4,547,324.

EXAMPLE I

Part A

A reactor was charged with N-phosphonomethyl-2-oxazolidone made from 0.025 mole of 2-oxazolidone by the process described in U.S. Pat. No. 4,547,324. The product was in the form of a viscous oil. This was heated together with 10 ml of water at 200° C. with stirring at 200 r.p.m. for a total of four hours.

The product was fractionated by liquid chromatography and proved to contain a 77.4% yield of N-phosphonomethylethanolamine and 9.6% of its cyclic internal ester, and a 5% yield of N-phosphonomethyl-2-oxazolidone. All of these yields are based on the starting material, 2-oxazolidone.

The fractions were recombined, stripped to an oil, and heated with 5 g (0.125 mole) of sodium hydroxide, 5 ml of water and 0.1 g of cadmium oxide. This was a 5:1 equivalent ratio of sodium hydroxide to starting 2-oxazolidone. The heating was conducted at 225° C. for 80 minutes and the reaction mixture was acidified with hydrochloric acid to form the free acid and separated on a Dowex 50X8-400 ion exchange column with water. The amount of glyphosate obtained was 3.6 g representing a yield of 85.7% based on 2-oxazolidone.

Part B

This illustrates the advantage of the process of the invention over that of U.S. Pat. No. 4,547,324. The following conditions are duplicated from those described in Example 3 of that patent.

A 100 ml. Monel autoclave was charged with the stripped reaction product oil from the phosphonomethylation of 0.025 mole of 2-oxazolidone; 5 g (0.125 mole) of sodium hydroxide, 25 ml of water; and 0.325 g of cadmium oxide. Thus, the reaction mixture contained a 5:1 molar ratio of alkali to oxazolidone derivative. The autoclave was heated at 260° C. for one hour. The pressure rose to 700 psi during the heatup (½ hr.) and remained constant through the reaction period. The reaction product was acidified with HCl and separated on a Dowex 50X8-400 ion exchange column with water. On analysis by proton NMR, the yield was found to be 40.2% of N-phosphonomethylglycine and 29.2% of aminomethylphosphonic acid based on 2-oxazolidone starting material.

Part C

This Example illustrates that the process of U.S. Pat. No. 4,547,324 can be improved by operating under more advantageous temperature conditions not taught in that patent while using less cadmium oxide catalyst, and by increasing the alkali to oxazolidone molar ratio. These reaction conditions are described in copending U.S. patent application Ser. No. 823,177 filed on even date with this application.

The same reactor as used in Part B was charged with 6.07 g of the same stripped reaction product oil from the phosphonomethylation of 0.0265 moles of 2-oxazolidone as is used in Parts A and B; 7.44 g (0.186 mole) of sodium hydroxide (7:1 molar ratio of alkali to 2-oxazolidone); 4.26 ml. of water and 0.1 g of cadmium oxide.

The reactants were heated for 2 hours, 10 minutes at 225° C. and the reaction products were isolated and analyzed in the same way as described in Parts A & B. This showed that the reaction product 81.9% of N-phosphonomethylglycine and 4.6% yield of aminomethylphosphonic acid based on 2-oxazolidone.

Thus the adjusted conditions had clearly reduced the by-product formation but there was still a significant shortfall in production of N-phosphonomethylglycine. In addition in Part C, 7 moles of sodium hydroxide were required as opposed to the 5 moles used in Part A.

It will be readily appreciated then that the process of the invention results in significant advantages over that taught in the prior art as represented by U.S. Pat. No. 4,547,324.

EXAMPLE 2

This Example demonstrates the hydrolysis step carried out in a solution containing sulphuric acid.

A reactor was charged with the same stripped product oil as was used in Example I starting with 0.025 moles of 2-oxazolidone, 0.123 g (5 mol %) of sulphuric acid and 10 ml of water. This reaction mixture was heated at 175° C. for four hours.

The product was separated by liquid chromatography on a Dowex 50X8-400 ion exchange resin column with water. The first fraction proved to be unreacted starting material (10% yield), the second (6.4%) was the cyclic internal ester of N-phosphonomethylethanolamine, and the third (76.3% yield) was found to be N-phosphonomethylethanolamine.

This hydrolysis in the presence of an acid with a non-nucleophilic anion yields a good conversion to the ethanolamine derivative that can thereafter be oxidizd using the techniques described above.

EXAMPLE 3

This Example demonstrates the effect of the presence of sodium carbonate on the efficiency of the catalyst in the oxidation of N-phosphonomethylethanolamine to glyphosate.

Part A 4.0 G (0.026 mole) of N-phosphonomethylethanolamine were reintroduced into a reactor along with 4.13 g (0.103 mole) of sodium hydroxide, (4:1 molar ratio of alkali to oxazolidone), 4.13 g of water and 0.1 g of cadmium oxide. The reactor was closed and heated at 225° C. for one hour.

Product was isolated by liquid chromatography and analyzed by proton NMR spectroscopy. This showed that the reaction product comprised 94.5% of N-phosphonomethylglycine and 3.5% of aminomethylphosphonic acid.

Part B

A reactor was charged with 4.0 g (0.026 mole) of N-phosphonomethylethanolamine, 4.13 g (0.103 mole) of sodium hydroxide, 2.73 g (0.026 mole) of sodium carbonate, 4.13 g of water, and 0.1 g of cadmium oxide. The reactants were heated at 225° C. for one hour. Separation and analysis of the components of the reaction mixture after acidification with dilute hydrochloric acid as in Part A, showed 75.2% yield of glyphosate and a 6.3% of aminomethylphosphonic acid and 14.0% of unreacted N-phosphonomethylethanolamine.

Thus, the effect of sodium carbonate which would be formed during the hydrolysis reaction in the presence of sodium hydroxide, is a significant depression of the level of conversion to the desired product when compared with operation in the absence of sodium carbonate.

EXAMPLE 4

This Example illustrates the use of catalysts other than cadmium oxide in the oxidation phase of the reaction in the absence of sodium carbonate. This is in surprising contrast to the teachings of U.S. Pat. No. 4,547,324 which permits only the use of cadmium oxide.

In each case of 4.0 g (0.026 mole) of N-(phosphonomethyl)ethanolamine, 4.13 g (0.103 mole) of sodium hydroxide, 4.13 g of water and the indicated amount of catalyst were used. The reaction temperature in each case was 250° C. and product separation and analysis were as described in Example 3.

| Catalyst | | Reaction | Conversion | |
|---|---|---|---|---|
| Nature | Amount | Time | Glyphosate | AMPA* |
| 5% PdO/Carbon | 0.15 g | 0.75 hr | 73.9% | 13.1% |
| Cu metal | 0.1 g | 2.0 hr | 62.4% | 16.4% |
| Zn metal | 0.1 g | 1.0 hr | 75.7% | 14.1% |
| ZnO | 0.1 g | 1.25 hr | 71.1% | 14.9% |
| CuO | 0.1 g | 2.0 hr | 67.2% | 16.2% |
| 1% PtO/Carbon | 0.3 g | 1.0 hr | 76.7% | 15.7% |

*Aminomethylphosphonic Acid

The N-phosphonomethylglycine which is the desired end product of this reaction is a highly important herbicide with very attractive and broad applications. The present invention describes a critical step in an attractive route to the production of this commercially significant product.

What is claimed is:

1. A process for the production of N-phosphonomethylglycine which comprises reacting an aqueous solution of N-phosphonomethyl-2-oxazolidone so as to bring about hydrolysis of the oxazolidone group and formation of carbon dioxide; continuing the reaction till the oxazolidone has been converted to N-phosphonomethylethanolamine or the cyclic internal ester thereof and removing the carbon dioxide co-product; thereafter oxidizing the hydrolyzate by adding a greater than one molar excess, after neutralization of acid groups in the phosphonomethyl group, of an aqueous alkali and a catalyst selected from cadmium, copper, zinc, palladium and platinum and their respective salts, oxides and hydroxides; heating at a temperature of from 200° to 300° C.; and, acidifying the reaction mixture to generate N-phosphonomethylglycine.

2. A process according to claim 1 in which the N-phosphonomethyl-2-oxazolidone is hydrolyzed at 100°-270° C. in an autoclave under autogenous pressure.

3. A process according to claim 1 in which the catalyst is cadmium oxide or cadmium hydroxide.

4. A process according to claim 1 in which the oxidation reaction is conducted at a temperature of from 200 to 250° C.

5. A process according to claim 1 in which the oxidation reaction employs sodium hydroxide in a molar ratio to the hydrolyzate after neutralization of the acid groups in the phosphonomethyl group of from 1.5:1 to 6:1.

6. A process according to claim 1 in which hydrolysis of the oxazolidone group takes place in the presence of a catalytic amount of an acid.

7. A process according to claim 6 in which the acid catalyst is sulphuric acid.

8. A process according to claim 7 in which the hydrolysis reaction takes place at 100°-300° C.

9. A process for the preparation of N-phosphonomethylglycine which comprises hydrolyzing an aqueous solution of N-phosphonomethyl-2-oxazolidone by heating at 175°-250° C. in an autoclave under autogenous pressure; removing carbon dioxide formed during the hydrolysis; adding to the reaction mixture a stoichiometric excess of sodium hydroxide in a molar ratio to the hydrolyzate after neutralization of the acid groups in the phosphonomethyl group, of 1.5:1 to 4:1, and a catalytically effective amount of cadmium oxide and thereafter heating the reaction mixture at a temperature of 200°-250° C. in the autoclave, so as to oxidize the hydrolyzate to the tri-sodium salt of N-phosphonomethylglycine; and upon completion of the oxidation reaction, liberating the free acid from the salt by the addition of acid.

* * * * *